(12) United States Patent
Gerbaulet et al.

(10) Patent No.: US 11,045,166 B2
(45) Date of Patent: Jun. 29, 2021

(54) ULTRASOUND PROBE AND DEVICE FOR 3D IMAGING OF THE JAW

(71) Applicant: TROPHY, Marne la Vallee (FR)

(72) Inventors: Jean-Pierre Gerbaulet, Boulogne-Billancourt (FR); Jean-Marc Gregoire, Mettray (FR); Franck Levassort, Saint-Avertin (FR)

(*) Notice: Subject to any disclaimer, the term of this patent is extended or adjusted under 35 U.S.C. 154(b) by 200 days.

(21) Appl. No.: 14/440,233

(22) PCT Filed: Nov. 7, 2013

(86) PCT No.: PCT/EP2013/073299
§ 371 (c)(1),
(2) Date: May 1, 2015

(87) PCT Pub. No.: WO2014/072427
PCT Pub. Date: May 15, 2014

(65) Prior Publication Data
US 2015/0313572 A1 Nov. 5, 2015

(30) Foreign Application Priority Data

Nov. 8, 2012 (FR) .................................. 1260617

(51) Int. Cl.
*A61C 9/00* (2006.01)
*A61B 8/08* (2006.01)
(Continued)

(52) U.S. Cl.
CPC .......... *A61B 8/0875* (2013.01); *A61B 5/0088* (2013.01); *A61B 5/4542* (2013.01);
(Continued)

(58) Field of Classification Search
CPC ....... A61B 8/0875; A61B 8/4494; A61B 8/58; A61B 8/54; A61B 8/483; A61B 8/5207;
(Continued)

(56) References Cited

U.S. PATENT DOCUMENTS 6,638,219 B1 * 10/2003 Asch ..................... A61B 8/00
433/214
7,285,093 B2 * 10/2007 Anisimov ............ A61B 8/0875
600/443
(Continued)

FOREIGN PATENT DOCUMENTS

| FR | 2962926 | 1/2012 |
|---|---|---|
| WO | WO 95/04506 | 2/1995 |
| WO | WO 2008/137030 | 11/2008 |

OTHER PUBLICATIONS

International Search Report dated Jan. 16, 2014 for International Application No. PCT/EP2013/073299, 3 pages.
(Continued)

*Primary Examiner* — Matthew Nelson

(57) ABSTRACT

This invention concerns an ultrasonic dental imaging probe (1), typically comprising several transducers (4) arranged to operate as a transmitter and a receiver, and in particular arranged to transmit ultrasonic waves at a frequency of at least 10 MHz, and optionally several transducers (4) arranged to operate as a transmitter and a receiver and arranged to transmit ultrasonic waves at a frequency of less than 4 MHz. The transducers are mounted on a flexible support (3), secured to a rigid frame (2) typically in a "U" shape. The invention also concerns a device comprising one such probe.

17 Claims, 6 Drawing Sheets

(51) Int. Cl.
*A61B 8/00* (2006.01)
*A61B 5/00* (2006.01)
*A61C 19/04* (2006.01)
*B06B 1/06* (2006.01)

(52) U.S. Cl.
CPC .......... *A61B 5/4547* (2013.01); *A61B 8/4227* (2013.01); *A61B 8/4416* (2013.01); *A61B 8/4444* (2013.01); *A61B 8/4494* (2013.01); *A61B 8/483* (2013.01); *A61B 8/5207* (2013.01); *A61B 8/54* (2013.01); *A61B 8/58* (2013.01); *A61C 9/0086* (2013.01); *A61C 19/04* (2013.01); *B06B 1/0622* (2013.01); *A61B 2562/066* (2013.01); *A61B 2562/164* (2013.01)

(58) Field of Classification Search
CPC ... A61B 8/4444; A61B 8/4416; A61B 8/4227; A61B 5/0088; A61B 5/4547; A61B 5/4542; A61B 2562/164; A61B 2562/066; A61C 9/0086; A61C 19/04; B06B 1/0622
USPC .......................................................... 433/29
See application file for complete search history.

(56) References Cited

U.S. PATENT DOCUMENTS

| | | | | |
|---|---|---|---|---|
| 8,622,937 | B2* | 1/2014 | Weng | A61B 8/12 600/439 |
| 2008/0242979 | A1* | 10/2008 | Fisher | A61B 6/4233 600/427 |
| 2010/0256496 | A1* | 10/2010 | Zhu | A61B 5/0091 600/459 |
| 2012/0244489 | A1* | 9/2012 | Carnahan | A61B 8/0875 433/25 |
| 2013/0109963 | A1* | 5/2013 | Zhu | A61B 8/0825 600/427 |
| 2013/0301380 | A1* | 11/2013 | Oraevsky | A61B 8/5215 367/7 |

OTHER PUBLICATIONS

M.C.D.N.J.M. Huysmans et al., "Ultrasonic measurement of enamel thickness: a tool for monitoring dental erosion?," Journal of Dentistry, 28, 2000, pp. 187-191.

Hans-Peter Müller et al., "Ultrasonic determination of thickness of masticatory mucosa: A methodologic study," Oral Surgery Oral Medicine Oral Pathology, vol. 88, No. 2, Aug. 1999, pp. 248-253.
Jeffrey A. Ketterling et al., "Design and Fabrication of a 40-MHz Annular Array Transducer," IEEE Transaction on Ultrasonics, Ferroelectrics, and Frequency Control, vol. 52, No. 4, Apr. 2005, pp. 672-681.
Jeffrey A. Ketterling et al., "Operational verification of a 40-MHz annular array transducer," IEEE Trans Ultrason Ferroelectr Freq Control, vol. 53, No. 3, Mar. 2006, pp. 623-630.
Kuo-Ting Wu, Development of Integrated and Flexible Ultrasonic Transducers for Aerospace Applications, Dept. of Electrical and Computer Engineering, McGill University, Nov. 2010, 260 pages.
Xuefeng Zhuang, et al., "Flexible Transducer Arrays with Through-Wafer Electrical Interconnects Based on Trench Refilling with PDMS," IEEE, 20$^{th}$ International Conferences on MEMS, 2007, Hyogo Japan, 4 pages.
C.R. Bowen, et al., "Flexible piezoelectric transducer for ultrasonic inspection of non-planar components," Ultrasonics, vol. 48, 2008, pp. 367-375.
Rahul S. Singh et al., "Simulation, Fabrication, and Characterization of a Novel Flexible, Conformal Ultrasound Transducer Array," 2007 IEEE Ultrasonics Symposium, pp. 1824-1827.
Marielle Defontaine, et al., "A Prototype of a 500kHz Ultrasonic Matricial Device: Beam Scanner," 1999 IEEE Ultrasonics Symposium, pp. 1585-1588.
Iyad Al Haffar et al., "Experimental evaluation of bone quality measuring speed of sound in cadaver mandibles," Oral Surgery, Oral Medicine, Oral Pathology, Oral Radiology, and Endodontology, vol. 102, No. 6, Dec. 2006, pp. 782-791.
P. Laugier, "In Vivo Ultrasound Assessment of Skeletal Status: Principles and Techniques," Journées Os-Ultrasons, Compiègne Jan. 24-25, 2002, 2 pages.
Pei-Jarn Chen et al., "The measurements of ultrasound parameters on calcaneus by two-sided interrogation techniques," Meas. Sci. Technol., vol. 16, 2005, pp. 1349-1354.
Rimon Adel Messiha Tadross, "A Novel Imaging System for Automatic Real-Time 3D Patient-Specific Knee Model Reconstruction Using Ultrasound RF Data," University of Tennessee, Knoxville, May 2012, 345 pages.
European Search Report from EP Application Serial No. 18198363.6 dated Nov. 2, 2018; 12 pages.
Sherif, Ashraf F, et al., "Laser-Induced Photothermal Technique Used for Detection of Caries Human Tooth", Article in Proceedings of SPIE—The International Society for Optical Engineering—Mar. 2008; 10 pages.

* cited by examiner

ULTRASOUND PROBE AND DEVICE FOR 3D IMAGING OF THE JAW

CROSS REFERENCE TO RELATED APPLICATIONS

This application claims the benefit of and is a U.S. National Phase filing of PCT Application PCT/EP2013/073299 filed Nov. 7, 2013 entitled "ULTRASOUND PROBE AND DEVICE FOR 3D IMAGING OF THE JAW", in the name of Gerbaulet et al, which claims the benefit of French Patent Application No. 1260617 filed Nov. 8, 2012, all of which are incorporated herein in their entirety.

TECHNICAL FIELD

This invention concerns an ultrasonic dental imaging probe. It also relates to a dental imaging apparatus comprising such a probe, and a dental imaging method using such a probe.

Such a device allows a user to measure the profile of the supporting dental bone of an individual, its bone quality and included structures.

STATE OF THE PRIOR ART

A lengthier life span and the growing concern to provide seniors with an active and comfortable life has caused an increase in interest in dental implants. Today, no one wants to have a "device" in his mouth, be they dentures, false teeth or the equivalent, the fixation of which is uncertain, hygiene delicate and life limited, but nevertheless at an elevated cost. The alternative solution that has been developed worldwide is laying individual prosthetic dentures attached to artificial roots: Dental implants.

The installation of dental implants is a delicate surgical operation which requires adherence to an exacting standard on the part of the practitioner who performs it.

Prior to installation, the practitioner usually opens the gum at the location of the future implants to release the bone. Using one or more bits, he pierces the bone creating an insertion shaft, having a diameter that is slightly less than that of the implant that is designed to accommodate. The implant, generally consisting of titanium, is then inserted into the shaft and the gum is closed. What follows is a passive phase called the "integration period", during which the bone heals around the implant. This phase of healing, also called "osseointegration", may last from several weeks to several months.

It is followed by screwing the crown on the implant.

The definition of the drilling axis in order to obtain a precise final orientation of the implant, and the determination of the diameter and depth of the insertion shaft, are major difficulties in the installation of dental implants. Thus, sometimes the wall of the sinus is crossed or the dental nerve is affected by the drill bit when it is oriented improperly or goes too far into the jawbone.

Therefore, the correct implant placement has long been reserved for a minority of practitioners known for their skill, although operating empirically, and whose rates were generally high.

Since the 90s, techniques have been developed to enable most dentists to install implants while controlling risks. These are grouped under the name of computer-assisted implantology. Here is the principle.

From 3D images giving information about the patient's dentition and underlying structures (bone, nerve, sinus), the implantologist is able to plan and simulate the surgery using a computer program that stores 3D images of the implants and prosthetic abutments used. This results in realistic, accurate and reliable planning, including the required number of implants, their size and position, as well as the selection of appropriate prosthetic abutments.

The dentist then replicates this simulation during surgery, for example using a resin molding of the patient's jaw wherein drilling guides are incorporated in accordance with the simulation performed. This single use device, called "Surgical Guide" is precisely adapted to the case being treated. Drill-stops limit the depth of the drilled holes to complete the system.

It is possible to achieve a similar result using a process called "navigation" in which the practitioner's hand is accurately guided by an optical, computer and possibly robotic system.

Cost of Computer-Assisted Implantology

Until recently, the high cost of implants prevented coverage of this prosthesis by health and mutual insurance, which has made dental implantology inaccessible for the majority of patients. By becoming more widespread, the ability to offer completely safe computer assisted implantology should change that, as long as the price of the implant decreases substantially.

Even if we can hope that increased competition will lower prices of materials and of practitioners, it is not the same for 3D imaging, which is essential to this surgical technique and that currently uses X-ray scanners: "Helical (Spiral)" or CT scanner and "cone beam" or CBCT.

For example, in 2011, CT images taken at a radiology center in France would cost from € 150 to 450 depending on the material and whether the image was a partial or total view of the jaw.

Today, despite a strong breakthrough of CBCTs in the offices of some importance, 3D imaging could be an obstacle to the democratization of the computer-guided implantology, because its cost is high (about 100,000 euros to purchase a CBCT).

Moreover, for offices not equipped with a CBCT, subcontracting the review exam may prolong processing times, sometimes excessively so in areas where the scanners are few.

In less developed countries, the barrier to 3D imaging is even higher because the scanners are more scarce and the cost of the images is proportionately higher.

From an economic and practical point of view, 3D imaging is one of the weak links in the chain of technology needed for wide dissemination of guided implantology. Therefore, an inexpensive device, installed in an office, would have some benefit for the economics of public health.

The Irradiation From the 3D X-ray Imaging (RX)

There is yet another problem to be raised regarding 3D imaging using X-rays: the radiation dose to which the patient is subject. To rebuild a 3D image, a scanner requires a large number of 2D images. Therefore, while the irradiation corresponding to a conventional panoramic radiography is approximately 15 mGy (milligray), that of a dental scan is between 200 and 400 mGy!

Studies conducted in 2007 in the United States (Amy Berrington de Gonzalez et al, Rebecca Smith-Bindman et al) showed that the tumor risk due to exams using X-rays (radiation-induced cancers) is significant, especially if exams are repetitive. But these tests have grown exponentially in recent years.

According to Longstreth et al, five dental radiographic assessments increase the risk of developing an intra-cranial meningioma.

According to five epidemiological studies by Preston-Martin and White, salivary gland and cranial tumors are associated with cumulative radiation of dental diagnostics.

According to Hallquist et al, radiation due to examinations of the face and skull, especially dental x-rays, induce an increased risk of cancers of the thyroid.

A study by Memon et al shows that the occurrence of thyroid cancer is directly related to taking dental radiographs.

Since 2005, significant penetration has been achieved by CBCTs in dental offices (there are now 25 manufacturers), mainly in implantology offices, but because of the autonomy afforded to the practitioner, it has not solved the problem as might have been hoped. In fact, a series of articles published in the New York Times in 2010 condemned the excessive use of CBCTs in dental, implantology, orthodontics offices, and even in pediatrics.

Even if the doses are less than those emitted during similar tests with traditional scanners (helical (spiral) scanners), Dr. John Ludlow, at the University of North Carolina's Dental School, showed that a CBCT delivers between 4 and 67 times more radiation than the digital panoramic radiographs, consistent with the figures quoted above. Health authorities in several countries therefore recommend minimizing doses as much as possible to patients when using X-rays, without recommending abandonment. Indeed, rejecting diagnostic imaging is no longer conceivable in our time.

Using Ultrasound

In 1999 Muller presented a paper describing how to measure the thickness of the masticatory mucosa with specific commercially available equipment ("Ultrasonic determination of thickness of masticatory mucosa", Oral Surgery Oral Medicine Oral Pathology, vol. 88 No. 2, August 1999). This apparatus is produced under the brand name KRUPP and is called SDM. It consists of a small pen probe with a tip bent to facilitate its placement on the gum, and has a transducer with an active diameter of 4 mm. It indicates that this equipment makes it possible to measure the thickness of the gum at a point manually set by the practitioner. But this type of device is not satisfactory for a practitioner wishing to schedule a surgery with sufficient accuracy.

In 2001, the Israeli company, Imadent filed a patent (U.S. Pat. No. 7,285,093) concerning a system resembling ultrasound tomography.

But this technology is not satisfactory for a practitioner wishing to schedule a surgery with sufficient accuracy. Since then, the patent has been abandoned.

The purpose of this invention is to provide a device with little or no irradiation, that can be used as a 3D imaging apparatus (for example to provide a dentist images enabling him to plan his surgery), and preferably with sufficient resolution and/or at a cost that will make it possible to install and operate in an interesting way by a practitioner in a dental office.

PRESENTATION OF THE INVENTION

This object is achieved with an ultrasonic dental imaging probe, comprising:
means for transmitting ultrasonic waves, arranged to emit ultrasonic waves at a frequency of at least 10 MHz (preferably at least 15 MHz). This means of ultrasonic wave emission will comprise a flexible ultrasonic array comprising:
several "high frequency" transducers arranged to operate in transmission and reception, and in particular arranged for transmitting ultrasonic waves at a frequency of at least 10 MHz (preferably at least 15 MHz), and arranged in array form
a flexible substrate upon which the "high frequency" transducers are mounted,
a rigid frame secured to and in contact with the flexible ultrasonic array, so that each "high frequency" transducer is arranged to transmit an ultrasonic wave in a direction opposite (preferably perpendicular) to the rigid frame, typically in the direction of the bone to be imaged.

Preferably, each "high frequency" transducer is arranged to transmit an ultrasonic wave in a direction perpendicular to the surface of the flexible support carrying the "high frequency" transducer.

Preferably, each "high frequency" transducer is arranged to transmit an ultrasonic wave in a direction opposite (preferably perpendicular) to the surface of the flexible support carrying the "high frequency" transducer.

Preferably, the rigid frame is secured to and in contact with the flexible support of the array (but preferably not in contact with "high frequency" transducers) so that the flexible support conforms to the shape of the rigid frame.

The means for transmitting ultrasonic waves are preferably further arranged to transmit ultrasonic waves at a frequency of less than 4 MHz, the flexible ultrasonic array will preferably further comprise several "low frequency" transducers also carried by the flexible support and arranged to operate as a transmitter and a receiver and arranged to transmit ultrasonic waves at a frequency of less than 4 MHz and mounted to the flexible support so that each "low frequency" transducer is arranged to transmit an ultrasonic wave in a direction opposite (preferably perpendicular) to the rigid frame, typically in the direction of the bone to be imaged.

Preferably, each "low frequency" transducer is arranged to transmit an ultrasonic wave in a direction perpendicular to the surface of the flexible support carrying the "low frequency" transducer.

Preferably, each "low frequency" transducer is arranged to transmit an ultrasonic wave in a direction opposite (preferably perpendicular) to the surface of the flexible support carrying the "low frequency" transducer.

Preferably, the rigid frame is secured to and in contact with the flexible support of the array (but preferably not in contact with "low frequency" transducers) so that the flexible support conforms to the shape of the rigid frame.

The flexible support may be mounted so that it is detachable from the rigid frame for interchangeability of the rigid frame.

Preferably, the rigid frame is in a curved form ("U-shaped") having a concave side surrounding a central axis and a convex side, the curved shape being defined by two side edges facing each other and connected by a bottom, the flexible support being secured to the rigid frame of the concave side of the rigid frame. The two side edges are preferably remote from the concave side, by a distance of between 8 mm and 30 mm, or between 4 cm and 20 cm.

The bottom may have at least one cutout area which makes its width, measured in a direction parallel to the central axis, less than the width of the side edges.

Each of the two side edges and the bottom of the rigid frame are preferably secured to a part of the ultrasonic array, upon part of which the transducers are mounted (both the "high frequency", and the "low frequency" transducers, if the probe includes them).

A transducer is a device that converts a physical quantity into another.

The transducers of the probe according to the invention are arranged to, in case of the "receiver", convert an acoustic wave (ultrasound) to another physical quantity, and in case of the "transmitter" convert that other physical variable into an acoustic wave (ultrasonic).

The transducers (both "high frequency" and "low frequency" transducers if the probe includes them) are preferably electro-acoustical elements (preferably of the piezoelectric type) or another (for example, acousto-optical transducers) and/or may optionally be interwoven with optical waveguides.

Electro-acoustical characterizes all systems or any material capable of generating an acoustic wave (sound or ultrasound) from an electrical signal and/or vice versa, all system and material capable of generating an electrical signal from a wave or acoustic signal. Ceramics and piezoelectric films, the cMUTs are examples of electroacoustical systems.

Electro-acoustical characterizes all systems or any material capable of generating an acoustic wave (sound or ultrasound) from an electrical signal and/or vice versa, all system and material capable of generating an electrical signal from a wave or acoustic signal.

The transducers (both "high frequency" and "low frequency" transducers if the probe includes them) are preferably arranged in a linear array of elementary transducers, at one or two dimensions forming one surface or three-dimensional, forming one surface or one volume.

According to yet another aspect of the invention, a dental imaging device is proposed, comprising:

A probe according to the invention,

Control means for the probe, and

Means to process the signals coming from the probe.

The device in accordance with the invention may comprise a means for connection between the probe and the means of control, the connection means may be disconnected and re-connected to disconnect a first type of probe from the means of control and to re-connect a second type of probe to the means of control.

In accordance with yet another aspect of the invention, a first method to use a device according to the invention is proposed, characterized in that a probe according to the invention is mounted inside the mouth by coating the gum on a toothless zone or by covering one or more of the teeth and their gums. The "high frequency" transducers of the probe preferably emit ultrasonic waves at a frequency of at least 10 MHz (preferably at least 15 MHz) and optionally the "low frequency" transducers of the probe, if it includes them, may transmit ultrasonic waves at a frequency of less than 4 MHz.

According to yet another aspect of the invention, a second method of use for a device according to the invention is proposed, characterized in that a probe according to the invention is placed outside the mouth surrounding all or part of a maxillary or mandibular arch, or two parts of a jaw at the same time. Preferably, the "low frequency" transducers of the probe emit ultrasonic waves at a frequency of less than 4 MHz, and/or the "high frequency" transducers of the probe may transmit ultrasonic waves at a frequency of at least 10 MHz.

According to yet another aspect of the invention, a method of using a device according to the invention is proposed, characterized in that it implements both the first and second methods of use according to the invention respectively inside and outside the same mouth with two different types of probes.

According to another aspect of the invention, a method for calibrating a probe according to the invention is proposed, wherein the transducers of the probe are operated to transmit and receive while the flexible ultrasonic array surrounds a gauge immersed in a coupling liquid. The gauge preferably includes acoustical benchmarks (hollows, hole(s), bump(s), groove(s), and/or inclusion(s)).

DESCRIPTION OF THE FIGURES AND EMBODIMENTS

Other advantages and specifications of the invention will appear upon reading the detailed non-limiting description of implementations and embodiments, and the following drawings attached:

FIG. 1 illustrates a device 51 according to the invention comprising a "Type 1" or "Type 2" probe 1;

FIG. 2 illustrates a "Type 1" probe according to the invention straddling the gum 7, FIG. 3 illustrates a "Type 1" probe according to the invention straddling the gum 7, FIG. 4 illustrates a "Type 1" probe according to the invention straddling the gum 7, FIG. 5 illustrates a "Type 1" probe according to the invention straddling a tooth and its gum 7, FIG. 6 illustrates a "Type 2" probe according to the invention, FIG. 7 illustrates an electronic module of a device according to the invention, FIG. 8 is a cross-section view of the profile of a "Type 1" probe according to the invention, straddling the gum 7, and used in the "high frequency" mode, ("reflective" mode for a high resolution definition view of the bone profile)

These implementations and embodiments are non-limiting, variants of the invention may be considered in particular with only a selection of the features described and subsequently isolated from the other characteristics described (even though this selection is isolated within a sentence comprising these other characteristics), if the selected characteristics are sufficient to provide a technical advantage or to distinguish the invention over the state of the prior art. Preferably, this selection comprises at least one functional characteristic without structural details, or with only a part of the structural details if only this portion is sufficient to provide a technical advantage or to distinguish the invention from the state of the prior art.

First described, in reference to the FIGS. 1 to 11, is a device 51 according to the invention.

The device 51 makes it possible to obtain a 3D image of the jawbone 8, maxillary and/or mandible of a person, using ultrasound to determine the dimensional characteristics and the mechanical properties of the bone 8.

Overall Architecture of the Device 51

Figure 1:
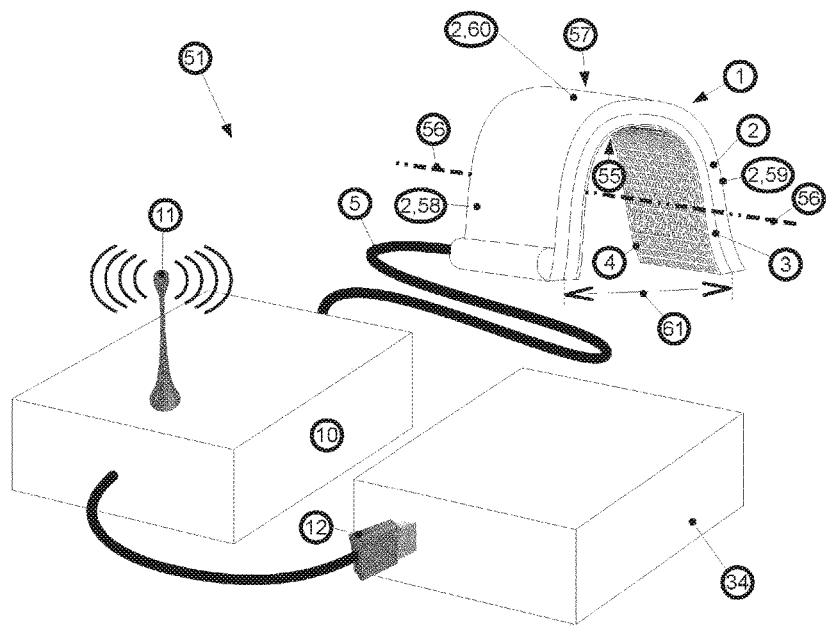
Figure 2:
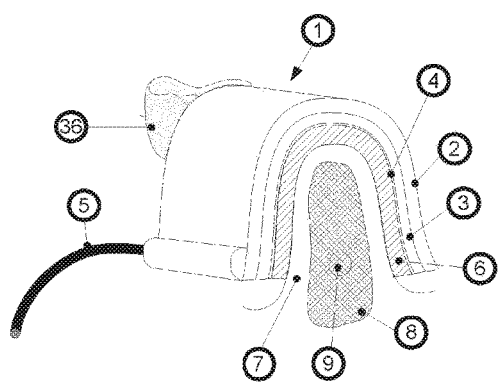

As shown in FIG. 1, the device 51 comprises:

A probe 1, preferably interchangeable,

An electronic power supply module 10, for controlling the probe and acquisition of data or signals from the probe 1, and A processing module 34 for data or electronic signals from the sensor.

Figure 3:
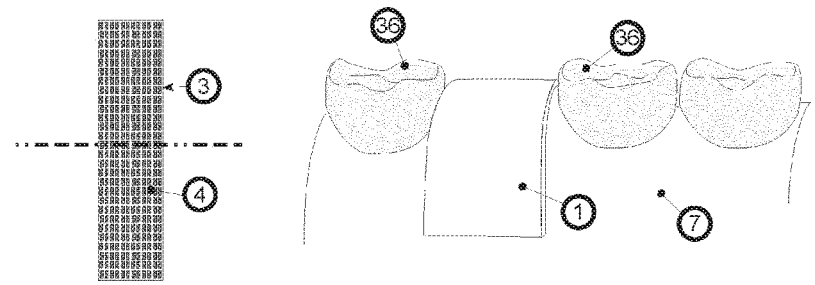
Figure 4:
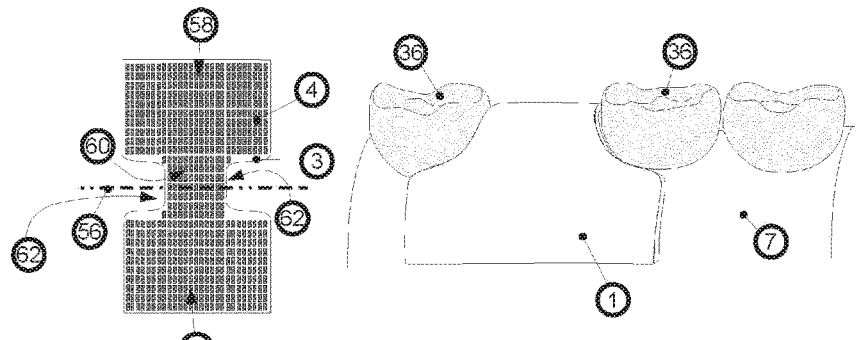
Figure 5:
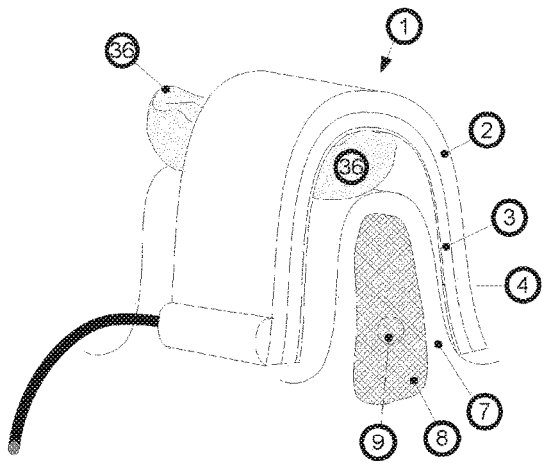
Figure 6:
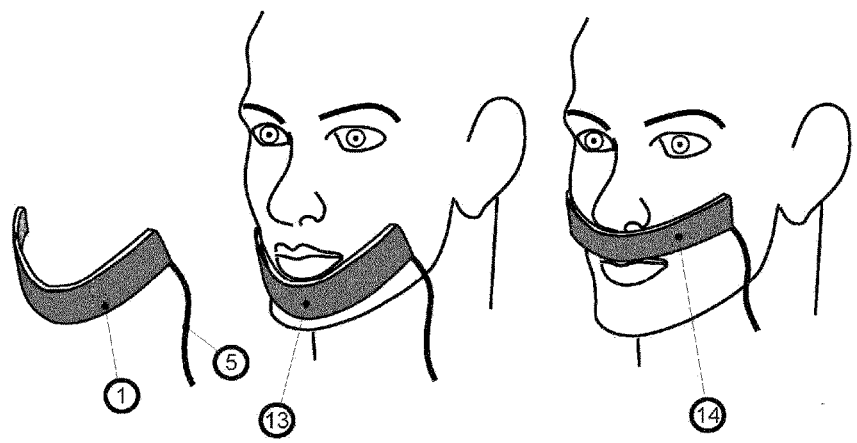
Figure 10:
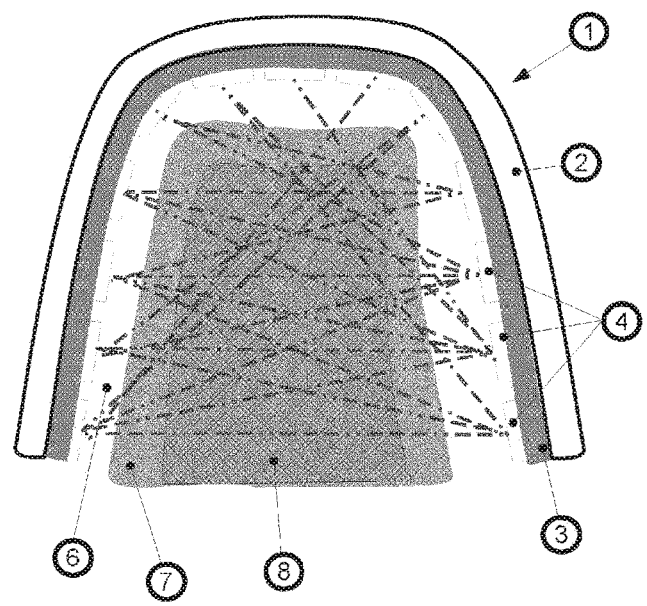
FIG. 10 is a cross-section view of the profile of a "Type 1" probe according to the invention, straddling the gum 7, and used in the "low frequency" mode, ("transmissive" mode for a tomographic type reconstruction))
Figure 11:
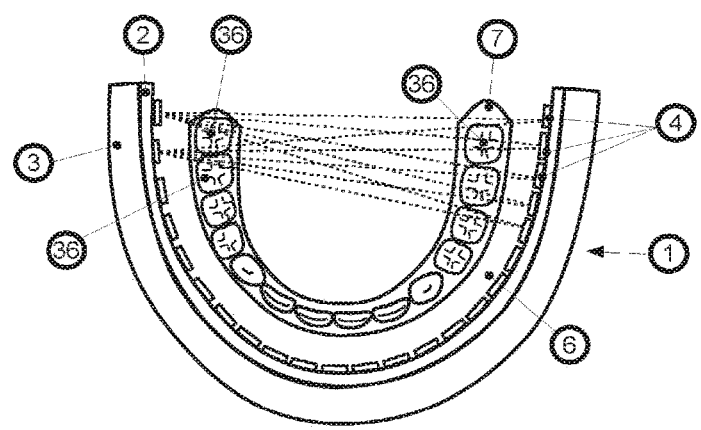
FIG. 11 is a cross-section view from above a "Type 2" probe according to the invention, straddling the jaw, and used in the "low frequency" mode, ("transmissive" mode for a tomographic type reconstruction)

Probe 1 is:

either, a specific "type 1" probe 1, intended to be used within the mouth (of an animal, preferably a human being), which covers the gum 7 (as illustrated in FIG. 2, 3, 4, 8 or 10), or a tooth 36 and the gum 7 (as shown in FIG. 5), through an acoustic coupling material 6, or a type 2 probe (as shown in FIG. 6, or 11) that encompasses all or part of the jaw, and is used outside 13, 14 of the mouth, The signals obtained by the probe 1 during the measurements are transmitted to the module 34, preferably including a digital system, for example a PC computer, by means 11 of LAN wireless connection, WIFI or other, or by means 12 of wireless or wired connection such as cable, for example of the USB type, imposing an additional constraint of electrical insulation to meet the safety standards for electromedical devices, or of the optical (fiber) type to simplify compliance with insulation rules.

Specific software installed on the module 34, for example on a PC computer, can control and configure the electronic module 10.

Structure of the Ultrasonic Probes

Type 1 and 2 probes are constituted by:

means for transmitting ultrasonic waves, arranged to emit high frequency ultrasonic waves at a frequency of at least 10 MHz (preferably at least 15 MHz, preferably at between 15 MHz and 25 MHz). This means of ultrasonic wave transmission will comprise a flexible ultrasonic array 3, 4 comprising:

Several "high frequency" transducers 4 arranged to operate as transmitter and receiver, and in particular arranged to transmit ultrasonic waves at a frequency of at least 10 MHz, or even at least 15 MHz, preferably at between 15 MHz and 25 MHz (that is to say, that each of these "high frequency" transducers will preferably have a bandwidth of −6 dB Fsup-Finf, of its impulse response, centered on a central frequency (Fsup+Finf)/2 of at least 10 MHz, or even at least 15 MHz, preferably between 15 MHz and 25 MHz).

a flexible support 3 upon which are mounted the "high frequency" transducers 4 so that each "high frequency" transducer 4 is arranged to transmit an ultrasonic wave in a direction 16 opposite and perpendicular to the surface of the flexible support 3 carrying this "high frequency" transducer 4, a rigid frame 2 secured to the ultrasonic array 3, 4 and in contact with the flexible support 3 of the array but not the "high frequency" transducers 4, obtained for example by means of a resin shell, a means of connection 5, wired or wireless, to the electronic control module 10, said means of connection 5 may be disconnected and re-connected from the module 10 to disconnect a first type of probe and re-connect a second type of probe. This makes it possible to use a "Type 1" or "Type 2" probe, and it also allows for the use of different sizes or shapes of "Type 1" probes or different sizes or shapes of "Type 2" probes.

In this document, 1 MHz represents a frequency of 1 mega Hertz, i.e., $10^6$ Hertz.

The means for transmitting ultrasonic waves are preferably further arranged to transmit ultrasonic waves at a frequency of less than 4 MHz, preferably between 0.5 MHz and 4 MHz. The flexible ultrasonic array 3,4 further comprising several "low frequency" transducers 4 arranged to operate as a transmitter and a receiver and arranged to emit ultrasonic waves at a frequency less than 4 MHz, preferably between 4 MHz and 0.5 MHz (that is to say, that each of these "low frequency" transducers will preferably have a bandwidth of −6 dB Fsup-Finf, of its impulse response, centered on a central frequency (Fsup+Finf)/2 of at least 4 MHz, preferably between 0.5 MHz and 4 MHz), and mounted on the flexible support 3 so that each "low frequency" transducer 4 is arranged for transmitting an ultrasonic wave in a direction 16 opposite and perpendicular to the surface of the flexible support 3 carrying the "low frequency" transducer 4.

Later in this document, when we speak of the "transducer(s)" (4), this will encompass by default the case of high-frequency transducers and low-frequency transducers.

Note that the "high frequency" and the "low frequency" transducers 4 are designed to also work as a receiver (to receive an echo for "high frequency" and to receive the transmission wave transmitted by another transducer that is situated substantially opposite for "low frequency"). The transmission and reception functions of a transducer 4 can be physically divided into two separate locations, so that for "low frequency" transducers and/or "high frequency" transducers, the probe according to the invention may comprise a transmission array interspersed with a receiver array.

Flexible should preferably be understood as being able to "deform under its own weight". For example, the flexible support 3 alone (i.e., devoid of its frame 2) is deformed under the action of its own weight, like a sheet of paper: laid flat on a table, it takes on a flat shape, but when supported by one of its edges and above the table, it flexes and bends under the action of its own weight.

Rigid should preferably be understood as not being able to "deform under its own weight". For example, the rigid frame 2 alone does not deform under the action of its own weight: placed on a table, it does not take the flat shape of the table but keeps its curved shape; when supported by one of its edges and above this table, it still maintains the same curved form, without visible distortion.

However, as the above examples involve forms developable in the interests of simplifying the explanation, the flexible and rigid forms with which the invention is concerned may be generated if necessary by 3D processes that achieve anatomical shapes that cannot be developed, or that are completely awkward.

The Flexible Ultrasonic Array 3 and 4

The support 3 is a plate provided with two opposite and parallel surfaces 53, 54. The transducers 4 are mounted on one surface 53 of the support 3; the other surface 54 of the support 3 is in contact with the frame 2.

Figure 8:
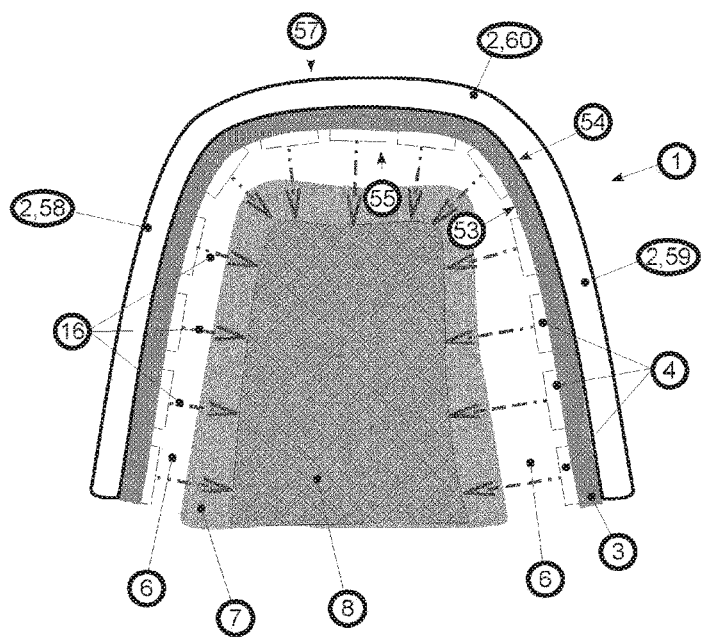

The multitude of small transducers 4 are fixed and distributed over the surface 53 of the support 3 to form a flexible array of ultrasonic elements of which the axes 16 of the acoustic beams generated by each element are perpendicular to the support surface 53 (as shown in FIG. 8).

The support 3 is located on the rear surface of the ultrasonic transducers 4; the ultrasonic transmission being on the front surface of the transducers which is in contact with the acoustic coupling 6.

Several ultrasonic array configurations are proposed.

The transducers 4 are preferably electroacoustic elements of the piezoelectric type or another.

The transducers 4 are preferably arranged in a linear array of elementary transducers, at one-dimensional or two-dimensional forming a surface.

The flexible support 3 preferably comprises a polymer film (e.g., polyimide) or silicone or a printed flex circuit configured to establish electrical connections.

The ultrasonic array 3,4 may, for example, be made from a polymer sheet or piezoelectric copolymer (PVDF, P (VDF-TrFE), or other) bonded to a flexible printed circuit (Flex) to play the role of the flexible support 3 in association with the "backing" (rear acoustic environment) required by the PVDF. The ultrasound elements are obtained by screen-printing the metallization on the transmitting surface of the piezoelectric polymer (front surface of the array) and by the screen-printing the printed circuit.

The ultrasonic array can also be achieved by combining the matrices integrated 1D or 2D, cMUT and/or piezoelectric polymers or copolymers (PVDF . . . ) and/or composites and/or piezoelectric ceramics. These mini arrays are produced from integrated circuit techniques and may comprise electronic multiplexing and preamplification. They are assembled on a flexible printed circuit ("Flex") which constitutes the formable support 3 and provides electrical connections. The array may also be produced by interwinding optical fibers or optical waveguides with small ultrasonic transducers 4, of the previously cited technology, to produce a photo-acoustic array. The optical waveguides emit an optical pulse in the gingiva parallel to acoustic beams and echoes produced at the interface are collected by the ultrasonic transducers 4, which operate as a receiver, in order to better discriminate the gum/bone interface signal.

In the case where the probe is used to make measurements through reflection of the thickness of the gum to make reconstruction of the jawbone profile possible. Each element generates an ultrasonic wave at a frequency of between 10 and 25 MHz.

In a preferred case, the transducers 4 may comprise transducers 4 capable of operating at low frequencies (0.5 to 4 MHz) and transducers 4 capable of operating at high frequency (10-25 MHz) which are:

either separate, but mixed and identically distributed on the surface 53 of the support 3, or combined, or even a broadband transducer able to transmit both low frequencies (0.5 to 4 MHz) and high frequencies (10-25 MHz). Notably, this is possible using cMUT technology (Dominique CERTON et al, METHOD AND DEVICE FOR GENERATION OF ULTRASOUND USING cMUTs AND METHOD AND SYSTEM FOR MEDICAL IMAGING. FR2962926). This configuration makes it possible to combine low-frequency components to perform measurements in transmission and high frequency components for reflection measurements of the thickness of the gum.

Thus, the device 51 shall preferably be implemented as:

first, a specific reflection imaging technique using high-frequency ultrasound (between 10 and 25 MHz) to determine, with a high resolution, the position and the shape of the bone 8 located under the gum 7, by performing measurements of the thickness of the gum 7 at a plurality of points by means of an array of ultrasonic transducers 4 positioned around the area in question; then perform a 3D reconstruction of the image from these measures, optionally in the form of the probe 1, and optionally of the image of the external anatomy of the oral cavity. And the 3D reconstruction of the bone profile 8 of the maxilla or mandible is obtained from a reflection measurement of the thickness of the gum 7 with ultrasonic frequency typically between 15 and 25 MHz. The use of such a range of high frequency and of an array of transducers 4 to multiply the points of measurement can significantly improve the resolution of the invention over the Prior Art. The probe 1 of the device 51 makes it possible to take measurements at many points, the position of each is precisely known from a calibration described below.

second, a technique using lower frequency ultrasound (between 0.5 and 4 MHz) as transmission, to define the density of the bone 8, which is quite variable in the mouth, as well as positioning the hollow structures included, such as the trajectories of nerves or sinus cavities. This type of image obtained by transmission with ultrasound frequencies between 0.5 and 4 MHz, makes it possible to determine the position of sensitive structures included in the bone 8, as well as the acoustic properties (speed and attenuation) of the cortical and alveolar bone that are good indicators of mechanical properties.

Each transducer 4 typically is in the form of a wafer (circular, square, rectangular . . . ) having an area of approximately 1 $mm^2$ or less in the case of imaging method B.

Following are given examples of manufacturing the transducers 4 on flexible support:

"Design and Fabrication of a 40-MHz Annular Array Transducer", Jeffrey A. Ketterling et Al., IEE transactions on ultrasonics, ferroelectrics, and frequency control, vol. 52, No. 4, April, 2005, "Operational Verification of a 40-MHz Annular Array Transducer", Jeffrey A. Ketterling et Al., IEE transactions on ultrasonics, ferroelectrics, and frequency control, vol. 53, No. 3, March, 2006, Thesis of Kuo-Ting Wu titled, "Development of Integrated and Flexible Ultrasonic Transducers for Aerospace Applications", McGill University, Montreal, November, 2010, "Flexible Transducer Arrays with through-wafer electrical interconnects based on trench refilling with PDMS", Xuefeng Zhuang, Der-Song Lin, Omer Oralklan, and Butrus T. Khuri-Yakub, E. L. Ginzton Laboratory, Stanford University, CA, USA, IEEE, $20^{th}$ international conferences on MEMS, 2007, Hyogo Japan.

"Flexible piezoelectric transducer for ultrasonic inspection of non-planar components", C. R. Bowen et al., Ultrasonics 48 (2008) p. 367-375, "Simulation, Fabrication, and Characterization of a Novel Flexible, Conformal Ultrasound Transducer Array", Rahul S. Singh et al., 2007 IEEE Ultrasonics Symposium.

The Rigid Frame 2

The array 3, 4 is secured to the rigid frame 2 which is:

initially conformable and capable of being rigidified (silicone resin, formable blade, thermoformable PVC sheet, etc.). In this case, the probes are configurable by the practitioner based on the patient's anatomy. In the case of custom probes, the ultrasonic array 3, 4 of a "type 1" probe may optionally be sterilized and reused. In this case, the frame, adapted to the anatomy of a given patient, cannot be reused for another patient.

or machined directly into its final form by a rapid prototyping process (milling, 3D printer) in a suitable rigid material, or even molded to an anatomical support (molding of the jaw, for example) in a fast-cure polymerizing resin or equivalent, all of these methods being known to those skilled in the art. In this case, the probes are factory built to establish a "range" of probes of different sizes and shapes. The type 1 probes made in the factory are typically designed to be reusable and must be sterilized by a suitable means. Type 2 probes, which are positioned outside of the mouth, are reusable.

In both cases, the production principle is the same, but in the case of a probe configurable by the practitioner, there must be a way to perform a calibration operation in the dental office, as described below. To freeze the calibration, the ultrasonic array must first be secured to a rigid frame of the same shape.

One means of creating the frame 2 for a type 1 probe involves a fast-cure polymerizing resin casting using a plaster cast of the jaw or mouth, and inserting the ultrasonic flexible array 4, 3 there between.

Other means of production involves using a 3D drawing software capable of rapid prototyping this frame 2.

Connecting or securing the ultrasonic array 3, 4 (specifically, the flexible support 3) to the frame 2 is carried out by clipping or by means of a mechanical, magnetic or other reversible process. Thus, the flexible support 3 is secured (for example by clipping, screwing or magnetization) to the frame 2 so that it becomes an integral part of the frame 2, but this attachment is reversible (for example, by unclipping or unscrewing or removing the magnetic elements) so that it can be removed from the rigid frame 2 to make it possible to interchange the "range" of probes of different sizes and shapes on the rigid frame 2.

The Rigid Frame 2 (and consequently the flexible support 3 when it is attached to the frame) has a curved "U-shape" having a concave side 55 surrounding a central axis 56 and a convex side 57, the curved shape being defined by two side edges 58, 59 facing each other and connected by a base 60, the flexible support 3 is secured to the rigid frame 2 on the concave side 55 of the rigid frame 2.

The ends of the two side edges 58, 59 are separated from the concave side 55, at a distance 61 of between 8 mm and 30 mm for a "Type 1" probe and between 4 cm and 20 cm for a "Type 2" probe.

Each of the two side edges 58, 59 and the base 60 of the rigid frame 2 are secured to a portion of the ultrasonic array 3, upon part of which are mounted the transducers 4.

Figure 7:
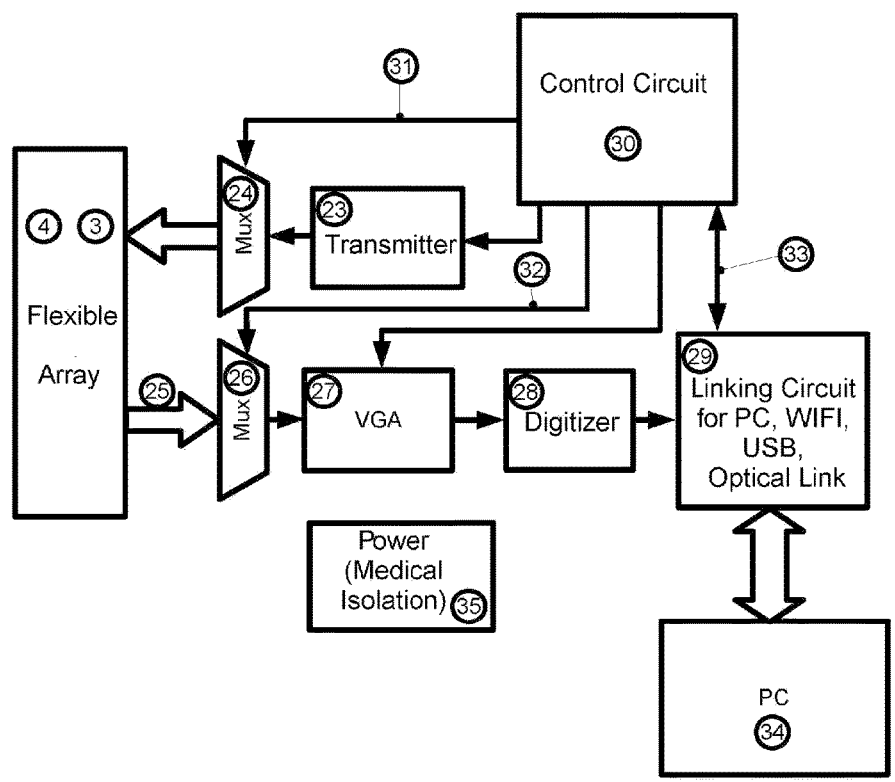

The Electronic Module 10 (FIG. 7)

The electronic module 10 includes a transmitting circuit 23 which generates an electric pulse excitation. This pulse is applied to one (or more) transducer element(s) 4 of the array 3, 4 via a selection system 24 (multiplexer, demultiplexer). Each transducer 4 thus excited emits a high frequency ultrasonic beam (above 10 MHz) or a low frequency beam (less than 4 MHz) according to the electrical excitation pulse and the transducer type. All transducer element(s) 4 may be selected to transmit individually or in groups, making the formation of an ultrasonic beam possible.

Some of the transducers 4 then receive echo waves in return (in receiver mode). One or more of the echo signals 25 thus transmitted from the transducers selected to act as a receiver 4, are sent to an amplification channel 27 whose gain is adjustable in function of time ("Time Gain Control" or TGC) via a selection circuit 26 (multiplexer, demultiplexer).

The output signal of this amplification chain is digitized by a scanner 28 and sent to the signal-processing module 34, which is of the microcomputer type, via a link path 29. This serial transmission 11, 12 may be through a USB, Ethernet or wireless connection, such as WIFI for example.

A control circuit 30 makes it possible to select transmission 31 and reception 32 of the transducer elements 4 of the probe 1. It assures the sequencing of the acquisition 33 in relation to the operator via the link path with the signal-processing module 34 (PC type).

It is perfectly feasible to incorporate some, or even all of this electronic system 10 in the probe 1, which is closest to the elements to improve the signal to noise ratio (or SNR or "Signal to noise ratio") and to reduce wiring. This circuit ensures the scanning of all ultrasonic transducers elements 4, to measure the dimensions of the biological elements (thickness of the gum 7), to reconstruct an image or analyze the signals to determine the acoustic properties of the bone 8 with the internal structures.

It is noted that the resulting ultrasonic signal is complex and consists of a multitude of echoes that arise in the gum tissue. Processing of the specific signal and several successive ultrasonic emissions (typically 10 to 5000, for a satisfactory averaging) are necessary to improve the signal to noise ratio and to precisely determine the positions of echoes produced at the entrance to the gum 7 and on the bone 8, and thus eliminate the artifacts.

Operation and Use of the "Type 1" Ultrasound Probe (FIGS. 2, 3, 4, 5, 8, 9 and 10)

In the case of the "Type 1" probe 1, the flexible ultrasonic array 3, 4 is positioned around the gum 7 and the acoustic coupling system 6.

The shape of the "Type 1" probe 1 is adapted to cover the gum 7 of a toothless area (as shown in FIG. 3 or 4), or the teeth 36 and the gum 7 before extraction, or on a limited area of a few teeth (as shown in FIG. 5).

For the "Type 1" probe, the actual ultrasonic array 3, 4 consists of a flexible support 3:

of a rectangular shape when laid flat (as shown in FIG. 3), or of a rectangular shape with two symmetrical cutouts 62 when laid flat (as shown in FIG. 4) to pass the gingival crest. The base 60 has at least one cutout area 62 (two on FIG. 4) which makes its width, measured in a direction parallel to the central axis 56, smaller than the width of the side edges 58, 59; or any other suitable shape for covering a toothless or otherwise portion of the jaw.

Figure 9:
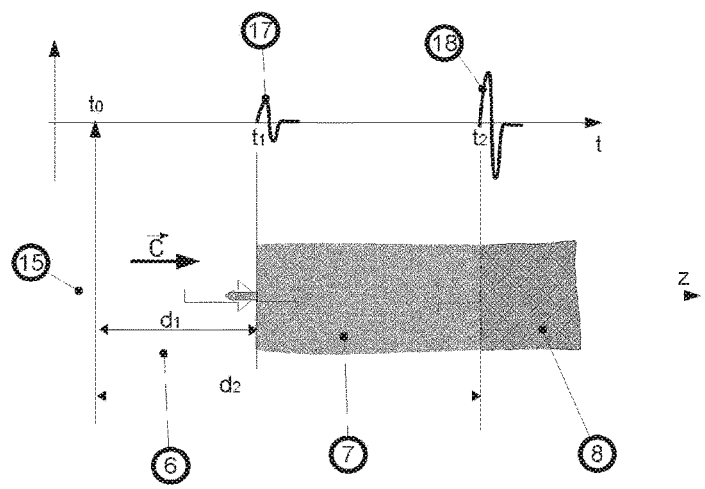
FIG. 9 illustrates the various waves and echoes during the use of a "high frequency" probe according to the invention.

The principle of operation for the "Type 1" probe 1 in reflective mode (high frequency transmission at greater than 10 MHz) is illustrated in FIGS. 8 and 9 and is the following (this principle is obviously transposable to the "Type 2" probe when it operates in "high-frequency" mode. In this case, the panoramic image so obtained is limited to the anterior surface of the bone and possibly the teeth).

"High frequency" transducers 4 each transmit an ultrasonic wave 15 at a t0 time instant successively. Each ultrasonic wave emitted by a "high frequency" transducer 4 spreads in a direction perpendicular 16 to the surface 53, to the flat emitting surface of the "high frequency" transducer and preferably on the surface of the gum 7. The ultrasonic signal collected by the same "high frequency" transducer 4 which has just transmitted, is a mode A-mode type signal (for "Amplitude Mode", or "Amplitude Mode", basic ultrasound mode, to differentiate it from another conventional B-mode ultrasound for "Brightness mode" or "Brightness Mode") for determining the distance between the echo 17 produced at time instant t1 at the entrance to the gum 7 and the echo 18 produced at time instant t2 by the bone 8, with the following ratio:

$$2(d2-d1)=C(t2-t1),$$

where C is the ultrasonic celerity (1500-1600 ms$^{-1}$) and where d1 and d2 are respectively the distances between the "high frequency" transducer 4 transmitting an ultrasonic wave and the gingival epithelium 7, firstly, and between the "high frequency" transducer 4 and the gum 7/bone 8 interface, secondly. The difference between d2 and d1, provides the thickness of the gum 7 on the bone 8.

The gum 7 is relatively thin (typically less than 10 mm). It is preferable to use of high frequency ultrasound, between 15 and 25 MHz, which is less penetrating and which are reflected almost entirely by the surface of the cortical bone 8. The advantage is short echoes are obtained for reconstructing 3D images of high axial resolution (better than 100 pm).

The acoustic coupling between the probe 1 and the gum 7 is provided by a flexible hydrophilic polymer or gelatin film 6 or any other system allowing the transfer of the ultrasonic energy with minimal losses between the front surface of the flexible array 3, 4 and the gum 7. The thickness, on the order of a few mm, compensate for the irregularities of the gum 7. To ensure an optimal acoustic coupling, the coupling must be a poor ultrasound attenuator and must be able to be coated on both sides with acoustic gel.

To allow measurements on different gum 7 morphologies, the device 51 may be used: either a probe with a frame formable by the practitioner, or a set of probes which have pre-calibrated curvatures and pre-set widths. The use of a probe 1 with a curvature that is formable by the physician allows a more precise adjustment to the gum and especially for limiting the number of probes stored to meet the variety of morphologies.

However, it requires the practitioner to perform a further measurement on a workpiece or a reference template (or "calibration phantom") or with an optical scanner, for example a laser scanner, to provide the reconstruction software with the geometric parameters of the probe 1 as well as the position and the transmission axis of each transducer (calibration data) to determine the position of the structures and to make an accurate reconstruction.

When this "type 1" probe further includes low frequency transducers generating waves capable of passing through the bone, it can operate on the principle of a transmission operation (not reflective) as explained in FIG. 10 and as explained below in the case of a "type 2" probe.

Operation and Use of the "Type 2" Ultrasound Probes (FIGS. 6 and 11)

In the case of the "Type 2" probe 1, the principle is essentially the same but the shape (always "U"-shaped) of the probe is slightly different in particular in its dimensions which are larger because the measuring field is greater.

The "Type 2" probe is intended to perform a comprehensive jaw tomography by transmission (as shown in FIGS. 6 and 11), which requires low frequency ultrasound having a frequency of between 0.5 and 4 MHz.

It is positioned outside of the oral cavity (cheeks, chin), and has a U-shape which encompasses the entire mandible or maxilla (as illustrated in FIG. 6). It requires application of an acoustic coupling gel 6 to the facial skin and placing an acoustic coupling device 6 on the mouth which may be of acoustic gel and/or gelatin or even water.

The probe 1 is produced according to the same principle as that of "Type 1", but its surface area is larger and its resolution is lower due to a lower ultrasonic frequency, for example 0.5 to 4 MHz, due to greater distance from the bone, and due to the use of the tomographic mode by transmission.

It also makes a panoramic description of the shape of the bone 8 possible by reflective high-frequency mode, for example from 10 to 15 MHz, on the principle described above in the case of a "Type 1" probe.

As the "Type 1" probe, its shape may be factory set and configured or adapted by the dentist to the patient's anatomy. The considerations concerning the practical embodiment of the "Type 1" probe therefore also apply to the "Type 2" probe.

Due to its position exterior to the oral cavity (on the bottom 13 or top 14 of the outside of the mouth), "Type 2" probe is more accessible, and its ability to cover the entire maxillary or mandibular arch makes it complementary to the "Type 1" probe.

Combined Use of Two Types of Probes

Therefore, there is a tendency to use both types of probes inside and outside of the same mouth according to the following method:

a "Type 1" probe is mounted within the mouth by covering the gum 7 of a toothless area inside that mouth or covering one or more teeth 36 and their gum 7 inside the mouth; the transducers 4 of the "Type 1" probe emit high frequency ultrasonic waves (of at least 10 MHz, preferably of at least 15 MHz, preferably between 15 MHz and 25 MHz) or low frequency ultrasonic waves (lower than 4 MHz, preferably between 0.5 MHz and 4 MHz), preferably of high frequency;

a "Type 2" probe is placed outside this same mouth surrounding all or part of a maxillary or mandibular arch of the mouth, or both parts of the jaw located within that mouth at the same time; the "Type 2" transducers 4 of this probe emit high frequency ultrasonic waves (of at least 10 MHz, preferably between 10 MHz and 15 MHz) or low frequency ultrasonic waves (lower than 4 MHz, preferably between 0.5 MHz and 4 MHz), preferably of low frequency; using two "Type 1" and "Type 2" probes is possible, thanks to their means of connection 5 which is disconnectable and reconnectable to the control means 10, that makes it possible to switch between the two types of probes.

This allows one to take a 3D tomography, at lower frequencies, of the cortical and alveolar bone of all or part of the jaw, with its internal structures, and to define their average and/or spot density at any point in the zone.

The high frequency ultrasonic waves make it possible, in reflective mode, to take an accurate measurement of the cortical bone profile on its front surface.

Signal Processing by the Module 34

The signals originating from the transducers and acquired by the data acquisition module 10 are processed within the data processing module 34, typically by a software implementing a signal processing method.

For a high frequency reflection operation, for example with the "Type 1" probe in FIG. 8, the software performs a reconstruction of the bone profile 8 located under the gum 7, from the signals transmitted by the electronic probe calibration data module 10, and, optionally, 3D data defining the shape of the gum 7. The signals transmitted by the electronic module 10, then consist of many point measurements, from the distance between the probe 4 and the cortical bone 8, make it possible to determine the thickness of the gum 7.

When probe 1 ("Type 1" or "Type 2") works at low frequency (as shown in FIG. 10 in the case of a "Type 1" probe or as shown in FIG. 11 in the case of a "Type 2"

probe), the software is capable of processing signals transmitted through the jawbone 8 to extract a parametric representation of its internal structure, by a ultrasound computed tomography technique ("A prototype of 500 kHz ultrasonic matricial device: beam scanner >> Marielle Defontaine et al., 1999 IEEE Ultrasonics Symposium; "Experimental evaluation of bone quality measuring speed of Sound in cadaver mandibles", Oyad Al Haffar et al., Oral Surgery, Oral Medicine, Oral Pathology, Oral Radiology, and Endodontology, vol. 102, No. 6, December, 2006; "In vivo ultrasound assessment of skeletal status: principles and techniques", P. laugier, Journées Os-Ultrasons, Compiègne 24-25 Jan., 2002; "The measurements of ultrasound parameters on calcaneus by two-sided interrogation techniques", Pei-Jarn Chen et al., Measurement Science and technology, vol. 16, 2005).

For a "Type 2" probe, the software mainly processes signals from the low frequency transmission of ultrasonic waves through the jaw and mouth, to perform a type of tomographic or scanned reconstruction. It also processes high frequency reflective signals transmitted by the probe, in order to produce a 3D profile of the maxillary or mandibular arch bone.

The software is made up of several programs whose complementary features are useful to a dental surgeon, for example in connection with dental implants.

The main function is to process the data supplied by the electronic system 10 to achieve 3D images of the bony structures of the jaw, and to extract information on their density.

It is provided by a program to detect the echoes produced:

at high frequency, to the gum 7 and bone 8 interfaces in order to determine the profile thereof (mode A signals localized in space);

at low frequency by the ultrasonic beams passing through the bone 8 to allow 3D reconstruction of the internal structures, to measure the acoustic velocity (celerity) parameters and attenuation to determine bone density parameters.

Raw data is generally very noisy, "segmentation" software is required to provide the relevant information for the practitioner.

Shaping the signals emanating from the electronic system 10 are each associated with 3D geometry (source and management point), following the calibration procedure. Thus, the initial data (ultrasound emission point, the direction of emission and echo distance) make it possible to determine a point cloud corresponding to the ultrasound imaged object. The software, by extracting the dimensional parameters of the probe 1, makes it possible to generate a 3D image. The software takes into account the speed of the ultrasound according to the media traversed.

This type of 3D reconstruction is known (thesis entitled "A novel Imaging System for Automatic Real-Time 3D Patient-Specific Knee Model Reconstruction Using Ultrasound RF Data").

The noise of ultrasound images generate multiple parasitic contours, extraction of 3D surfaces from these signals may require entering "prior knowledge" into the software. These methods are known by those skilled in the art. Their application requires processing related to knowledge of artifacts due to repeating echoes in stratified structures, or using models with multiple combinations generating the peculiarities of the area concerned from a single deformable bone model.

These 3D images are designed to be used in dental offices, replacing the RX scanner images, particularly during computer-assisted implant placement.

The device 51 may be:

used alone in an "ultrasound only mode" or associated with a multimodal configuration complementary to other conventional imaging techniques, with little or no radiation.

In the "ultrasound only" mode, the level of irradiation of patients is zero.

In the "multi-mode" setting, the software combines the images transmitted in accordance with the invention, with the images of at least one other complementary technique to create a 3D composite image of the gum 7, the teeth 36, and the cortical or alveolar bone 8, of the maxillary or the mandible. The contribution of these complementary techniques are adapted as appropriate. Thus, the at least one other complementary technique may include, for example:

an optical scanner of the oral cavity, which provides a 3D digital impression with accuracy of up to 20 pm, making it possible to establish anatomical references used to obtain a precise spatial resolution of the ultrasound image;

periapical and panoramic digitized X-ray images are merged with the ultrasound images to define the location of the structures including the sensitive structures, such as the alveolar nerve or sinus floor and the bone density.

The integration of the ultrasound data into a multimodal group to implement the other imaging techniques (periapical and panoramic ratios, digitizing the external surfaces . . . ), is taken into account. This specifically implies that the image formats from the ultrasound device are compatible with those images provided by the other techniques including DICOM images, commonly used in dental imaging, and other formats that may be encountered (STL, . . . ).

In the case of a multimodal use, using other imaging techniques, the software performs a fusion of a 3D ultrasound image and an image from one or more of the other techniques mentioned above.

These image mixing operations are well known to those skilled in the art.

A program makes it possible to evaluate the average or spot relative bone density (Hounsfield units) in the various areas concerned. As part of the multimodal protocol, the data on bone quality provided by other sources is merged with those of the ultrasound device.

The software further comprises a 3D drawing program of the acoustic array frame. This drawing is either produced from the calibration program, or comes directly from the image of the part provided by a 3D optical camera. It typically represents a frame 2 which is produced using a 3D printer, or a digital milling machine, both driven by the probe design software. The use of these probes are not surgical, so they may be made of non-biocompatible resins such as ordinary ABS.

Application For Planning the Placement of the Implant

The device provides 3D images and, more generally, the information necessary for a dentist using dental implant planning software to prepare his surgery in the area studied. The imaging device software 51 must therefore be able to interface with a planning software existing on the market, to provide images in the formats used in medical imaging.

As mentioned above, the "Type 1" ultrasonic probe, in a shape customized by the dental office, has great similarities in shape with the surgical guide itself. Therefore, the 3D drawing of such a guide can be produced by means of another 3D design program involving a drawing of the probe's shaft, the data provided by an implant planning software, position and axes of the drills guide cylinders particular.

Fabricating the guide, usually entrusted to a specialized plant or a prosthesis laboratory, may then be carried out in the office, following the same procedure as with the frame of the probe, but using a bio-compatible resin. The whole process greatly improves costs and the time required for computer-assisted implant placement.

The 3D imaging device, which is the object of this patent, may also be associated with virtual control systems called "navigation".

In practice, several types of marketable devices can be imagined. Here are two examples:

For radiology centers, hospitals and private and large dental offices, a self-contained unit, similar to the one proposed by Atys Medical for dermatology, which may possibly be portable, such as the Sonoscanner of Orcheolite. All the features described in the patent are offered by this device.

For the average dental office, maximally simplified equipment, may be reduced to a series of "Type 1" probes of the sizes and shapes mentioned, or a formable probe may be calibrated on a 3D model of the patient's jaw; these probes are connected to the USB port of a desktop PC with a specific image processing card, video output which is performed on the PC screen, and printouts on the printer associated with the PC.

Calibration of the Curvature and Shape of the Probe 1

Figure 12:
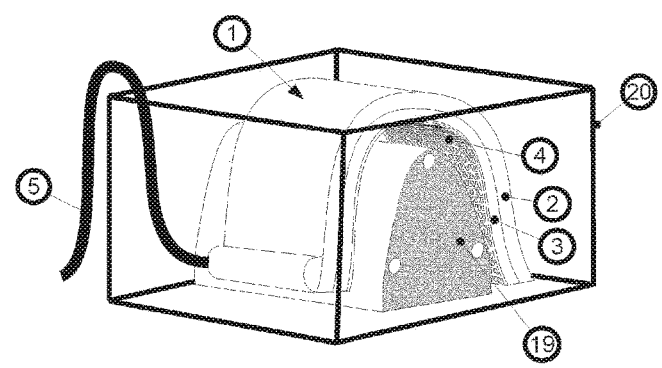
FIG. 12 is a view of a probe according to the invention straddling a calibration phantom, and during calibration.

For accurate reconstruction of the structures, the software needs to have the calibration data, that is to say for each transducer 4 that is a component of the ultrasonic array 3, 4 the spatial position of the acoustic beam (source and direction point). This information is obtained by measuring a calibration phantom 19 (that is to say a template as shown in FIG. 12, typically immersed in a tank 20 filled with a coupling liquid) or by using an optical, laser or other type of scanner, or a 3D intraoral camera. To do this, the probe's 1 transducers 4 are set to function as a transmitter and receiver in a device according to the invention, while the flexible ultrasonic array 3,4 surrounds the template 19 immersed in a coupling fluid.

When the curvature of the frame 2 and consequently that of the support 3 is factory preset, the calibration parameters or data is automatically supplied to the software (memory included in the probe 1 or in a parameter file).

Figure 13:
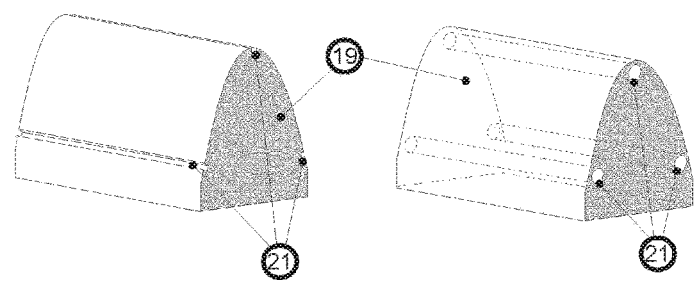
FIG. 13 illustrates two calibration phantoms.
Figure 14:
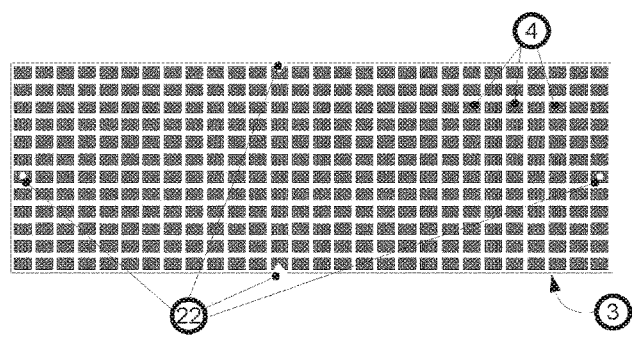
FIG. 14 illustrates the benchmarks 22 on the flexible array 3, 4 of a probe according to the invention.

When the curvature of the frame 2 and therefore of the support 3 is performed by the practitioner on the patient's jaw or on a plaster cast thereof, the calibration (FIG. 12) is formed in the office, for example on a calibration phantom 19 (typically in plastic) located in a small tank 20 containing an acoustical coupling liquid (typically water, or as a further option it may contain an antiseptic and/or antifungal agent). The calibration phantom 19 has a perfectly known shape and has acoustic register marks 21 such as hollows, hole(s), bump(s), groove(s), and/or inclusion(s) (groove on the outer surface of the template 19 in the example to the left in FIG. 13, or holes (cylindrical) within the template in the example to the right in FIG. 13) that makes it possible to identify the position of the transducers 4 with regard to these register marks. This information is necessary to determine the position in the space of each transducer 4 of the flexible array 3. In the case of a measurement of the curvature by an alternative method, optical camera or another, the flexible matrix 3, 4 has several register marks 22 (FIG. 14) adapted to the measuring method (hole, notch, screen printing or other) for precisely determining the position of each transducer 4 in space.

A calibration program is built in to the software of the device.

In summary, the device 51 is:
1) an ultrasonic device of sufficient resolution to be installed and operated in a way that would be of interest to a practitioner in a dental office;
2) a device that may be used as standalone 3D imaging equipment, or that may be associated with other low-ionizing imaging systems present in the office (or digitized periapical or panoramic radiography, optical scanner), or otherwise, to provide dentist images which will make it possible for him to plan his surgery;
3) a non-irradiating device,
4) a lower priced device than 3D imaging devices on the market, including CBCTs.

Of course, the invention is not limited to the examples that have been herein described and numerous modifications may be made without going outside of the scope of the invention.

For example, the probe 1 may incorporate all or part of the electronic control 10, excitation and pre-amplification of the flexible ultrasonic array, and/or all or part of the digitization of analog data and the transmission thereof, and or all or part of the electronics 34.

Of course, the different features, forms and variants and embodiments of the invention may be combined with each other in various combinations as long as they are not incompatible or mutually exclusive of each other. In particular, all variants and embodiments described above are combinable with each other.

The invention claimed is:

1. An ultrasonic probe (1) for dental imagery, comprising:
a flexible support;
means for transmitting ultrasonic waves mounted on the flexible support, the means for transmitting ultrasonic waves comprising,
a plurality of transducers to function in ultrasonic emission and reception, where the plurality of transducers emit ultrasonic waves of frequency from at least 10 MHz in a first mode, where the transducers are arranged in a prescribed arrangement on the flexible support;
a plurality of optical elements comprising optical waveguides mounted in a prescribed arrangement among the transducers on the flexible support and optical sources coupled to the optical waveguides, where an effect of optical emission by the optical waveguides is detected by ultrasonic reception at more than one of the plurality of transducers; and
means for signal processing data from the probe to generate 2D dentistry images and 3D dentistry reconstructions, where the means for signal processing uses data generated from the optical emission to discriminate a gum/bone interface.

2. The ultrasonic probe of claim 1, where the plurality of transducers and the optical waveguides are configured in an arrangement of linear segments with a length dimension, an arrangement of two dimensions forming a surface, or an arrangement with three dimensions forming a surface or a volume.

3. The ultrasonic probe of claim 1, further comprising a configured rigid reinforcement (2) the flexible support removably mounted to the rigid reinforcement so that the flexible support conforms to the shape of the rigid reinforcement, and where the rigid reinforcement does not deform under its own weight.

4. The ultrasonic probe of claim 3, where the rigid reinforcement (2) has a curved form presenting a concave side (55) surrounding a central axis (56) and a convex side (57), the curved form being delimited by two side edges (58, 59) laid out face to face and connected by a bottom (60), the flexible support (3) being secured to the rigid reinforcement (2) on the concave side (55) of the rigid reinforcement.

5. The ultrasonic probe of claim 1, where the means for transmitting ultrasonic waves is configured to operate in the first mode to generate a 2D surface image of at least one tooth and configured to operate in a second mode to generate a 3D reconstruction of internal structures of one or more teeth.

6. The ultrasonic probe of claim 5, where in the second mode, the transducers (4) function to emit ultrasonic waves of frequency lower than 4 MHz, where the internal structures include bone and nerve pathway, and where the 3D reconstruction includes gingiva adjacent the one or more teeth.

7. The ultrasonic probe of claim 1, further comprising:
means (10) for electronic communications with the probe, the means for electronic communications including wireless or wired transmission to and from the probe; and
means (30) for control of the probe including controlling the means for transmitting ultrasonic waves, characterized in that the means (10) for electronic communications comprises means for connecting (5) to the probe that is detachable to connect a first type of intra-oral probe (1) and is detachable to connect a second type of extra-oral probe (1).

8. The ultrasonic probe of claim 7, further comprising a plurality of detectable measuring elements at the flexible support to determine a 3D position of each transducer on the flexible support for each of the first type of intra-oral probe (1) and the second type of extra-oral probe (1).

9. The ultrasonic probe of claim 1, the probe (1) is adapted to operate inside a mouth to image a gum (7) on a toothless zone or to image one or more teeth and corresponding gum (7).

10. The ultrasonic probe of claim 1, where the probe (1) is adapted to operate outside a mouth to image whole or part of an upper dental arch or a lower dental arch, or to image whole or parts of both the upper and lower dental arch at the same time.

11. The ultrasonic probe of claim 1, further comprising a plurality of detectable measuring elements mounted at the flexible support to determine a 3D position of each transducer on the flexible support attached to a configured rigid reinforcement (2).

12. The ultrasonic probe of claim 11, where the plurality of detectable measuring elements comprises pins (22), holes, notches, or seriography.

13. The ultrasonic probe of claim 1, further comprising means for calibration for calibrating the probe using a calibration phantom or optical camera.

14. A method of using an ultrasonic probe (1) of dental imagery, the ultrasonic probe (1) including a flexible support (3), a plurality of transducers that includes at least electroacoustic elements to function in ultrasonic emission and reception, where the plurality of transducers (4) are arranged in a prescribed arrangement on the flexible support, and a plurality of optical elements comprising optical waveguides arranged among the transducers (4) on the flexible matrix and optical sources coupled to the optical waveguides, the method comprising:
transmitting ultrasonic waves of frequency from at least 10 MHz from a first subset of the electroacoustic elements (4) in a first reflection mode to generate a 2D surface image of at least one tooth;
transmitting ultrasonic waves of frequency of frequency lower than 4 MHz from a second different subset of the electroacoustic elements (4) in a second transmissive mode to generate a 3D reconstruction of internal structures of one or more teeth, where the internal structures include bone and nerve pathways, and where the 3D reconstruction includes gingiva adjacent the one or more teeth; and
emitting an optical pulse by a plurality of the optical waveguides and detecting the optical pulse emission by ultrasonic reception at a plurality of the transducers (4) in order to discriminate a gum/bone interface.

15. The ultrasonic probe of claim 1, where the plurality of the optical elements are configured to emit an optical pulse from the optical waveguides.

16. The ultrasonic probe of claim 15, where the optical pulse is parallel to acoustic beams.

17. The ultrasonic probe of claim 15, where echos generated by the optical pulse are collected by the plurality of the transducers (4).

* * * * *